United States Patent [19]

Sportoletti et al.

[11] Patent Number: 4,493,829

[45] Date of Patent: Jan. 15, 1985

[54] BIO-AVAILABLE SUCCINYLATED PROTEIN-IRON DERIVATIVES WHICH DO NOT CAUSE GASTRIC LESIONS, METHOD OF PREPARATION AND RELATED PHARMACEUTICAL COMPOUNDS

[75] Inventors: Giancarlo Sportoletti; Piergiuseppe Pagella; Pietro Cremonesi, all of Milan, Italy

[73] Assignee: Italfarmaco S.p.A., Milan, Italy

[21] Appl. No.: 469,282

[22] Filed: Feb. 24, 1983

[30] Foreign Application Priority Data

Mar. 2, 1982 [IT] Italy ................. 19908 A/82

[51] Int. Cl.³ ............................................. C07G 7/04
[52] U.S. Cl. .............................. 424/177; 260/112 R; 260/115; 260/121; 260/123.5; 260/112 B
[58] Field of Search ............... 260/115, 112 R, 121, 260/112 B, 123.5; 424/177

[56] References Cited

U.S. PATENT DOCUMENTS

| | | | |
|---|---|---|---|
| 2,932,589 | 4/1960 | Meyer et al. | 260/112 R X |
| 3,712,865 | 1/1973 | Evans et al. | 260/121 X |
| 3,756,682 | 9/1973 | Huber et al. | 260/115 |
| 3,764,711 | 9/1973 | Melnychyn et al. | 260/112 R |
| 3,873,296 | 3/1975 | Ashmead et al. | 424/177 X |
| 4,017,605 | 4/1977 | Huber et al. | 260/115 |
| 4,020,158 | 4/1977 | Ashmead et al. | 424/177 |
| 4,172,072 | 10/1979 | Ashmead | 260/115 |
| 4,208,405 | 6/1980 | Fouad | 424/177 |
| 4,216,144 | 8/1980 | Ashmead | 260/115 X |
| 4,411,915 | 10/1983 | Eriksson | 260/112 B |

Primary Examiner—Howard E. Schain
Attorney, Agent, or Firm—Walter H. Schneider

[57] ABSTRACT

The invention relates to succinylated proteins, with a degree of succinylation of between 20 to 100%, containing from 0.1 to 20% by weight of iron, obtained by treating succinylated proteins with iron salts in suitable pH ranges. The compounds in question, which are completely tolerated, are characterized by an optimum bioavailability of iron.

11 Claims, 9 Drawing Figures

BIO-AVAILABLE SUCCINYLATED PROTEIN-IRON DERIVATIVES WHICH DO NOT CAUSE GASTRIC LESIONS, METHOD OF PREPARATION AND RELATED PHARMACEUTICAL COMPOUNDS

The present invention relates to succinylated proteins, having a degree of succinylation of between 20 and 100%, containing from 0.1 to 20% by weight of iron, obtained by the treatment of succinylated proteins with iron salts at suitable pH intervals. The compounds involved, which are completely tolerated, are characterised by an optimum bio-availability of the iron.

Iron, which is present in all bodily tissues, plays a completely indispensable physiological role. It is part, and an essential component, of haemoglobin, myoglobin and the enzymes: catalase, fumaric-dehydrogenase, peroxidase, cytochromes, DPN-cytochromoreductase and metalloflavoproteins, such as ferroflavine. The tissues of an adult human body contain from 1.5 to 5 g of iron of which 60–65% is concentrated in the red blood corpuscles, whilst 18–30% is linked to the ferritin proteins and haemosiderin localised in the liver, spleen, bone marrow and cells of the endothelial reticular system. The remainder is distributed in the various enzyme systems mentioned above, in myoglobin (approximately 4%) and in transferrin (approximately 0.1%), the $\beta_1$ globulin for the haematic transportation of the iron of intestinal origin. It is capable of linking at physiological pH values, two iron atoms in a practically indissociable manner.

The iron requirement is satisfied in part by the use of endogenous iron (deriving from the destruction of old red blood corpuscles) and in part by the absorption of exogenous iron. The absorption of the exogenous iron takes place along the duodenum and the upper part of the jejunum and it is accumulated predominantly in the liver. The first pathological symptom of iron deficiency is hyperchromic sideropenic anaemia whose primary causes may vary: chronic haemorrhages taking place with gastroduodenal ulcers or neoplasia; deficient diets, or bad absorption as in the case with diarrhoea; increased requirements, for example in pregnancy, lactation, infectious diseases etc.; bad metabolic utilisation; particular treatments such as the administration of ACTH and cortisones.

The most suitable therapy is the administration of iron. This effectively reduces the anaemic condition when this condition derives from an actual iron deficiency. However, it is in general accompanied by undesirable side effects connected with the type of vector used for the iron. The most widely used pharmaceutical per os preparations are based on very varied organic and inorganic acid salts, gradually introduced into therapy in the hope of reducing the above-mentioned side effects. Per os specialities are therefore marketed based on inorganic salts of the type of: ferric chloride, ferrous sulphate, ferric phosphate, or even organic salts, such as, citrates, cholinates, aspartates, fumarates, gluconates, glycinates, lactates, oxalates, succinates. In the case of deep intramuscular administration the ferro-dextran complex is proposed whilst, for i.v. treatments (for sideropenic anaemia in which per os treatment has failed) use is made of the ferro-dextrin complex.

In the case of these latter types of complex the side effects may take the form of allergic reactions, temperature rises, tachycardia, leucocytosis, lymphadenopathy in the case of intramuscular treatment, and even anaphylactic shock, thrombophlebitis and circulatory collapse in the case of i.v. treatment. In the case of per os treatment using formulations based on the above-mentioned compounds, the side effects are in general gastrointestinal lesions, with necrosis and perforation of the mucous membranes in more serious cases, and diarrhoea and vomiting. In addition low tolerability makes the administration of suitable amounts of iron difficult. In order to minimise side effects it has been suggested that food should be taken at the same time, but this is in contradiction with the proven variability of absorption of the iron as a function of the composition of the foods themselves. It has in fact been ascertained that the absorption of the iron from preparations is optimum when the patient has fasted. In addition, gastric irritation is followed by the use of antacids which, in turn, reduce absorption and aggravate the anaemic state.

Considerable progress in iron therapy, particularly by per os administration, has been provided with the introduction onto the market of ferritin based specialities.

Ferritin is a ferric globulin and represents the most important iron-containing protein in the bodies of mammals. The commercial product is extracted from horse spleen as a raw material.

Its iron content is 20% in terms of dry weight. Its protein portion, apoferritin, has a molecular weight of approximately 445.00 and surrounds a "core" of crystalline oxide-phosphate iron. This is suitable for per os administration as it is soluble in water.

Ferritin based treatment does not result in the gastrointestinal side effects arising during the use of the above-mentioned iron derivatives. Its use is, however, restricted both as a result of the very high cost of the raw material and, in particular, as a result of the limited availability of sources of extraction.

The prior art appears to show that the optimum carrier for the iron for the purposes of absorption without side effects may be a protein carrier. Many proteins have a certain affinity for iron. Certain types of protein of animal origin (serum proteins, organ proteins, ovalbumins, lactoproteins) or vegetable origin (soya protein) have therefore been tested for use as carriers.

The interaction between inorganic ferric salts and the above-mentioned proteins leads to the formation of ferroprotein derivatives whose therapeutic interest is, however, undermined by a series of negative characteristics, including:

the insolubility of the derivatives obtained when the percentage of iron linked to the protein reaches values greater than 0.5%;

the difficulty or even the impossibility of evaluating what fraction of the total iron content, under such conditions of insolubility, is actually linked to the protein and what fraction is co-precipitated in the form of hydrated oxides which may cause severe gastric lesions;

the lack of homogeneity and compositional stability with respect to iron of these derivatives.

In addition, in the case of some proteins, including those derived from milk, the presence of soluble iron derivatives with a considerable amount of insoluble derivatives have been observed at various pH values, the composition of these soluble fractions being extremely variable as a function of very slight variations in the experimental parameters.

It has now been surprisingly ascertained that, by carrying out succinylation of the above-mentioned proteins under suitable conditions (the process normally used to obtain protein succinyl derivatives for use in foodstuffs or animal fodder) it is possible to obtain, by reacting these with iron, ferroprotein derivatives having a high iron content which are stable, soluble at pH values of more than 5, have diverse but reproducible iron contents, are able to supply iron to mammals when administered orally without causing side effects of the gastric lesion type. In rats, daily oral administration for 20 consecutive days did not provide evidence of any gastric lesions and had a high degree of tolerance.

In the case of rats, the comparison between conditions of sideraemia, after the oral administration of *equivalent* amounts of iron in the form of ferrous sulphate, horse spleen ferritin (Sigma, Saint Louis, Missouri) and ferroprotein derivatives from succinylated milk proteins, prepared as described in Example 1, showed that:
  (a) the haematic iron levels produced by the derivative of the present invention, with respect to those produced by ferrous sulphate, are prolonged in time (see Table IX);
  (b) the haematic iron levels produced by the derivative of the present invention, with respect to that of standard ferritin, are higher (approx. 1.5:1 on average) within the six hour period of the experiment (see Table X).

Bearing in mind the high degree of tolerability of the product, its low toxicity (greater than 4,000 mg/kg in Swiss mice), the high iron levels which may be obtained and the ease of supply of the raw material, the use of the derivatives of the present invention constitutes a clear improvement over the state of the art of iron treatments.

The physico-chemical characteristics of these succinyl ferroproteins, as mentioned above, are reproducible and stable as shown in the non-limiting examples. The absence of iron which is not linked is shown by the complete degree of solubility in an alkaline medium (conditions in which the iron ion is precipitated as hydrated oxide) of the preparations obtained from succinylated proteins and an iron salt.

The present invention therefore relates to derivatives, which have not been known up to now, characterised in that they contain amounts of iron which may vary as percentages, and amounts of animal or vegetable proteins which have been succinylated to various degrees, and in that they are designed to supply bio-available iron to mammals without causing gastrointestinal lesions when administered orally, as shown by the following Examples given by way of non-limiting references.

These derivatives may be used as the active principle in the preparation of pharmaceutical specialities for use in the treatment of anaemia caused by a lack of iron in mammals, this invention therefore also relating to any pharmaceutical form of administration containing these derivatives as the active principle for human or veterinary use.

The invention also relates to a method for the preparation of the succinyl ferroprotein derivatives characterised in that succinylated proteins are reacted (in a manner known per se) with iron ions at a pH of between 2 and 10 approximately, preferably at a pH close to neutrality, in aqueous solvents, and in that the products obtained are isolated from the reaction medium by precipitation at a pH in the range of 2–4, this latter pH range being provided spontaneously or by acidification. As an alternative, the reaction product may be isolated by the removal of the solvent after the pH has been adjusted to a value close to neutrality.

EXAMPLE 1

Preparation of 5% iron derivatives from succinylated proteins of whole milk powder 1 kg of milk powder was suspended in 6 liters of 0.3M sodium bicarbonate and, with mechanical stirring and pH control, 500 g of succinic anhydride were added in successive portions, the pH being maintained within a range of between 7.5 and 8 by means of the addition of 4N NaOH. After the addition, the mixture was stirred for 2 to 3 hours at ambient temperature. During this time the suspension was completely dissolved. The opalescent solution was centrifuged or filtered until almost clear and slowly acidified with HCl up to pH 3.

The precipitate formed was separated by centrifugation or filtration and re-suspended in water (approx. 8 liters). NaoH solution was added until it was completely dissolved (pH approx. 7.5). Centrifugation was carried out and the clear solution was re-acidified to pH 2.5–3 by means of the addition of HCl. The precipitate was recovered by filtration or centrifugation and washed with an HCl solution having a pH of 3. The residue, constituted by the succinylated proteins (whose degree of succinylation could be varied as a function of the amount of succinic anhydride used; in the case discussed here, this was 90% with respect to the groups which could be succinylated in the initial protein as given below) was, after drying under vacuum, dispersed in distilled water. It was dissolved by the addition of NaOH up to pH 7.5 diluting the solution such that the final protein concentration was aprox. 0.04 g/ml. A solution of an iron salt (for example $FeCl_3$) with a ratio of $Fe^{3+}$/succinylated protein of 1:10 by weight was added to this solution. This provided a suspension which was finely dispersed by means of mechanical stirring whilst the pH dropped to approx. 2.5. Stirring was continued for 3 hours at ambient temperature and the suspension was then filtered. The solid was suspended in water (approximately 3 volumes) and was dissolved by the addition of NaOH (pH 7.5).

The solution, which was not completely clear, was filtered and the product in the solid state recovered using one of the following methods:
  (a) the solution was acidified and the precipitate obtained at a pH of 2.5 was filtered off and dried under vacuum;
  (b) the clear solution was dialysed against water in order to eliminate the sodium chloride and then freeze-dried or dried by a spray dryer.

The finished product yields were the same and amounted to approximately 20% by weight of the initial powdered milk. The characteristics of the product are described in Table I (Example 1b).

EXAMPLE 2

Preparation of 5% iron derivatives from succinylated milk proteins

As described in Example 1, with the variant that the initial product was constituted by 350 g of milk proteins, previously precipitated from milk powder by dispersion of the powder in water (approx. 5 liters), acidification to pH 2.5 with a mineral acid and then filtration or centrifugation of the protein solid and drying.

The iron content, as given below (Table I), for the derivatives obtained in Examples 1 and 2 was approximately 4-5% by weight.

EXAMPLE 3

Preparation of iron derivatives from succinylated milk proteins having different iron contents The method steps described in Examples 1 and 2 were used with the same amounts of milk powder or previously precipitated milk proteins, whilst the $Fe^{3+}$/succinylated protein ratio by weight was modified to the values 0.1:10, 0.2:10, 0.5:10 and 1.5:10 providing iron derivatives whose characteristics are shown in Table I.

EXAMPLE 4

Preparation of iron derivatives from succinylated egg proteins (ovalbumin)

5 g of ovalbumin were dissolved in 100 ml of water containing 3 g of $KHCO_3$, and 2.5 g of succinic anhydride was added in successive portions to the clear solution whilst maintaining the pH at values of between 5 and 8 by the addition of NaOH. The mixture was left to react for 2 hours at ambient temperature. After acidification of the solution to pH 3.4 a precipitate was obtained which was isolated by centrifugation, purified by dissolution at pH 7.5 by NaOH and then re-precipitated at pH 3.4. The solid was recovered by centrifugation and dried under vacuum. The dry solid was suspended in distilled water and dissolved by the addition of NaOH (pH 8) so as to obtain a final solution of 0.04 g protein/ml.

A solution of salt of $Fe^{3+}$ (for example ferric chloride) was added to the very viscous solution so as to provide a ratio, by weight, of succinylated proteins/$Fe^{3+}$ of 10:1. In these conditions the pH dropped to 2.6 with the formation of a precipitate which was recovered by filtration. This precipitate was re-dissolved in water and NaOH was added until it was completely dissolved (pH 7.5). After dialysis against water, in order to remove the sodium chloride, the solid product was recovered by freeze-drying or by a spray dryer. The yield of the derivative was 33% by weight of the initial protein. Its iron content and characteristics are given in Table I.

EXAMPLE 5

Preparation of iron derivatives from succinylated proteins of bovine serum 1.5 g of $NaHCO_3$ were added to 50 ml of a solution of bovine serum proteins and the mixture was treated with 6 g of succinic anhydride added in successive portions, whilst the pH was kept between between the values of 7.5 and 8 by the addition of NaOH. When the addition was complete the reaction was left for 2 hours at ambient temperature and then a precipitate was produced by acidification to a pH of 2.4 by a mineral acid. The precipitate was recovered by centrifugation and purified as described in Example 4.

The solid product was suspended in water and brought to pH 7.5 by NaOH. The solution obtained in this way had added to it a solution of a salt of iron (III) (for example ferric chloride) until it reached a succinylated protein/$Fe^{3+}$ ratio by weight of 10:1. The pH dropped spontaneously to 2.4 and a precipitate which, when brought to pH 7.5, only dissolved in part, was obtained. The solution was separated from the residue by centrifugation, dialysis against water was carried out in order to eliminate the sodium chloride and freeze-drying was then carried out. The weight yield of the iron derivative, with respect to the initial protein, was approx. 30%. The iron content and characteristics are given in Table I.

EXAMPLE 6

Preparation of iron derivatives from succinylated proteins of pig liver 400 g of fresh pig liver was homogenized in a Silverson homogenizer in the presence of 800 ml of 0.2M $KHCO_3$ solution, pH 8.3. After centrifugation at 9000 rpm at 5° C., the supernatant was collected and filtered through a 0.45μ cellulose acetate membrane. 1.2 g of succinic anhydride was added in successive portions to 50 ml of clear solution, ensuring that the pH remained between 7.5 and 8 by the addition of NaOH.

The solution was left for 1 hour at ambient temperature and then acidified with mineral acid to a pH of 3 thereby obtaining a precipitate which was processed in the same way as in Example 4, with the modification that the final recovery was carried out by freeze-drying of the solution which had been dialysed against water.

The freeze-dried residue was suspended in water and brought to pH of 8 using soda. This provided a solution which was not completely clear and which was centrifuged. A solution of iron (for example ferric chloride) was added to the clear supernatant such that the (estimated) succinylated protein/$Fe^{3+}$ ratio was approximately 10:1.

The pH of the solution dropped to 2.6 providing a precipitate which was purified in the same way as in the previous Examples. The solid obtained from the freeze-drying of the final solution, dialysed against water, had the characteristics and iron content given in Table I.

EXAMPLE 7

Preparation of iron derivatives from succinylated soya proteins 5 g of soya proteins were suspended in 100 ml of water containing 3 g of $NaHCO_3$. The mixture was stirred until completely dissolved, the pH being maintained between 7.5 and 8 by the addition of NaOH and 2.5 g of succinic anhydride were added in successive portions. The mixture was stirred for two hours at ambient temperature and brought to a pH of 3.4 by the addition of mineral acid, thereby producing a precipitate which was purified in the same way as in the previous Examples. The solid residue of the final freeze-drying was suspended in 100 ml of water, the pH was corrected to 8 by the addition of soda and then the solution, which was not completely clear, was centrifuged.

The clear substance supernatant was treated with an iron solution (for example ferric chloride) such that the succinylated protein/$Fe^{3+}$ ratio was 10:1 by weight. The pH of the solution droppd spontaneously to 2.6 and a precipitate was formed and treated in the same way as in the previous Examples. The solid obtained from the final freeze-drying had the characteristics and iron content as given in Table I. The weight yeild with respect to the initial protein was 22%.

CHEMICO-PHYSICAL CHARACTERISATION OF THE IRON DERIVATIVES FROM SUCCINYLATED PROTEINS OBTAINED IN ACCORDANCE WITH EXAMPLES 1-7

The derivatives obtained in accordance with the above-mentioned Examples were analysed following the methods given below:

(a) Degree of succinylation

This characteristic was expressed as a percentage of the succinylated groups with respect to the groups capable of succinylation of the initial protein. The method described by S. Moore & W. H. Stein, J. Biol. Chem., 211, 907, 1954 was used, involving the reaction of the free amine groups with ninhydrin. The results are given in Table I.

(b) Iron content

The iron content was determined, either after hot extraction with 2N HCl or after complete digestion of the protein by sulphuric acid, as described in Standard Methods, 14th Ed., 1975, p. 208, APHA-AWWA-WPCF (reaction with o-phenanthroline). The values are given in Table I.

(c) Spectroscopic data (1) EPR spectroscopy

All the derivatives described in the above Examples showed the same spectroscopic behaviour. The EPR spectrum of the succinyl ferroprotein derivative prepared in accordance with Example 1 was plotted for example. The spectrum was recorded in freeze-dried powder and had a very wide signal, centered about $g=2.0$, with a signal amplitude of approximately 2000 G. A further well-resolved signal was present and was also centered around $g=2.0$. The shape of both the signals was characteristic of interacting $Fe^{3+}$ paramagnetic centres (F. Reid et al., Inorg. Chem. 7, 119, 1968). All these data showed the presence of protein structures closed around the linking agent.

2. Circular dichroism

The behaviour of the various derivatives described was also similar in this case. The circular dichroism spectrum of the succinyl ferroprotein derivative obtained in accordance with Example 1 was plotted for example. The spectrum was characterised by negative activity in the UV zone. This showed an intense negative band with a peak around 200 nm and a shoulder, also negative, centered around 225 nm. These spectral characteristics showed the predominance of a "random" protein structure (inter alia: F. Ciardelli & P. Salvadori—Optical Rotatory Dispersion and Circular Dichroism—Heyden & Son Ltd., London, 1973—Chapter 4.5).

3. UV-Visible absorption spectra

Figure 1:
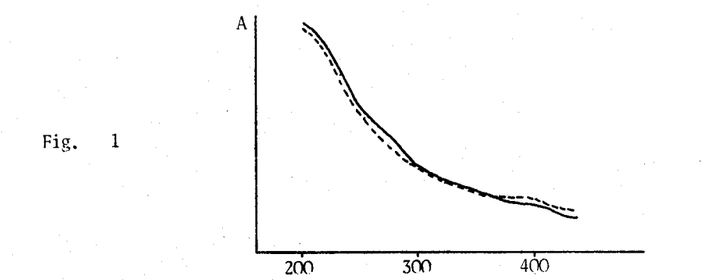

The behaviour with respect to the electronic spectrum of the various derivatives described was similar. FIG. 1 shows the UV-visible spectrum for the succinyl ferroprotein derivative prepared in accordance with Example 1.

The spectrum (continuous line) does not show absorption peaks but only a very weak shoulder around 450 nm. Under UV there was a fairly defined shoulder centered around 270 nm and a very intense absorption with a peak below 220 nm.

FIG. 1 also shows (dashed line) the spectrum of ferritin from horse spleen as a comparison (Boehringer-Mannheim).

The absorption spectra in the visible range are given in FIG. 1 and were carried out in water, pH 7. The spectrum of horse spleen ferritin under the same conditions is also given as a comparison (Boehringer-Mannheim).

4. Fluorescent Emission Spectrum

Figure 2:
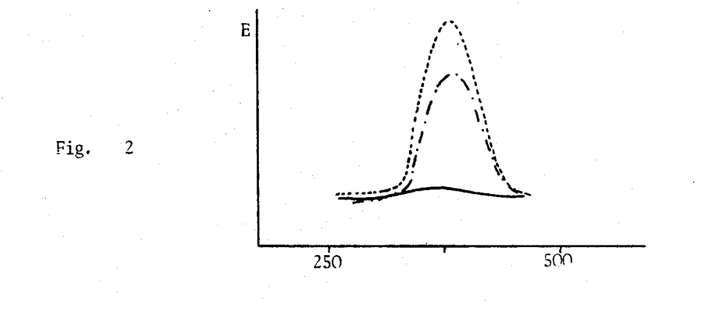

The fluorescent emission spectra are given in FIG. 2, in which the continuous line corresponds to the succinyl ferroprotein derivatives of the invention, the dot-dashed line to lactoproteins as such, and the dashed line to the succinylated lactoproteins.

Quenching of the fluorescence of the protein, due to the presence of metal, may be seen.

(d) Electrophoreses

The electrophoretic traces on cellulose acetate of the various derivatives in comparison with the succinylated proteins, the original proteins and ferritin are given in FIGS. 3 to 6.

Figure 3:
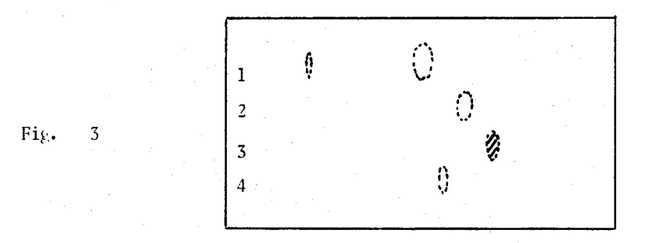
Figure 4:
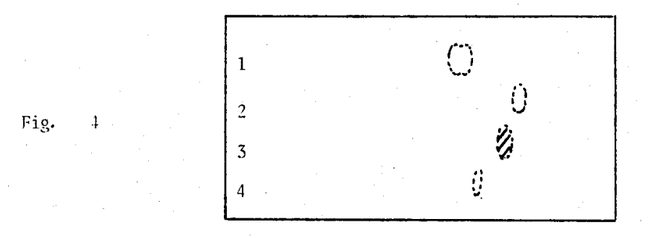

FIG. 3 shows the results of electrophoresis carried out on soya proteins (trace 1), succinylated soya proteins (trace 2), iron derivative of succinylated soya proteins (trace 3), iron derivative of non-succinylated soya proteins, soluble fraction (trace 4). FIG. 4 shows the results of electrophoresis carried out on ovalbumin (trace 1), succinylated ovalbumin (trace 2), iron derivative of succinylated ovalbumin (trace 3), iron derivative of ovalbumin (trace 4).

Figure 5:
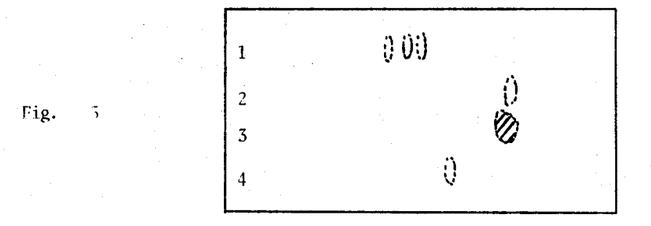
Figure 6:
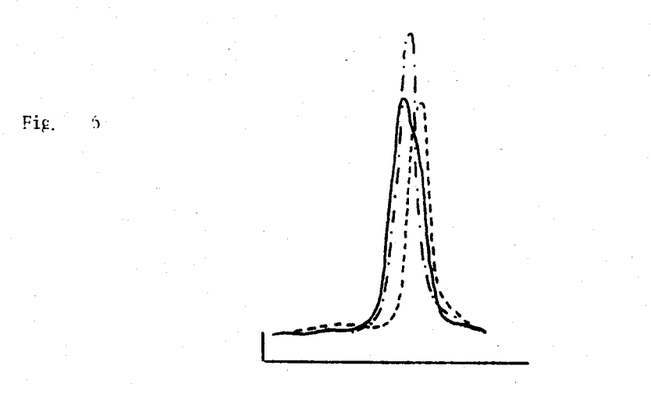

FIG. 5 shows the results of electrophoresis carried out on lactoproteins (trace 1), succinylated lactoproteins (trace 2), iron derivative of succinylated lactoproteins (trace 3), horse spleen ferritin (trace 4). FIG. 6 shows the results of electrophoresis (densitometric reading at 550 nm) carried out on the iron derivative of succinylated lactoproteins (continuous line), the iron derivative of succinylated soya proteins (dot-dash) and the iron derivative of succinylated ovalbumin (dashed line).

(e) Gel filtration

Figure 7:
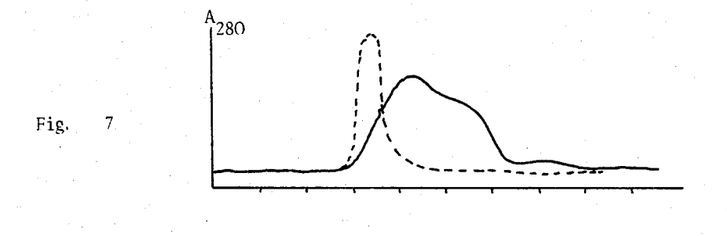
Figure 8:
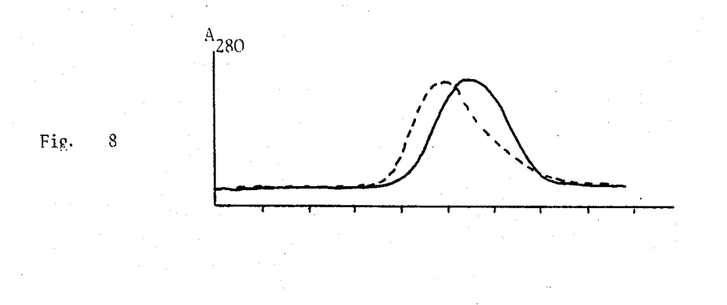

The gel filtration profile on Sephadex G 75 (Pharmacia, Uppsala) of the iron derivative of the succinylated milk proteins (obtained as described in Example 1), in comparison with the succinylated proteins themselves is given in FIG. 7, where the continuous line refers to succinylated lactoproteins, the dashed line to the corresponding iron derivative. The ordinate shows adsorption at 280 nm, and the abscissa the progressive number of fractions collected. It can be seen from the profile that the presence of iron causes a single output peak with a retention time similar to that of the column void. Bearing in mind that the molecular exclusion of Sephadex G 75 is approx. 75,000 Daltons, the apparent minimum molecular weight value of this aggregate is greater than this value. Moreover, in a different manner, a double peak with greater randomization was noted with the succinylated proteins. This factor was also observed in electrophoresis (FIG. 5). This type of behaviour shows that the iron present is a focus of intermolecular aggregation of the protein medium. Further data were extracted from the filter gel on Sephadex G 200 in comparison with ferritin (FIG. 8, in which the abscissa and ordinate are similar to FIG. 7, whilst the continuous line corresponds to the iron derivative of succinylated lactoproteins and the dashed line relates to ferritin obtained from horse spleen). In this case as well the peak was unambiguous whilst the retention time was greater than that of ferritin. This would appear to show that the apparent molecular weight is lower than that of the ferritin from horse spleen.

(f) Stability in gastric juice

This test was carried out on the iron derivative obtained from Example 1 and was carried out by dissolving 25 mg of the derivative in 0.5 ml of distilled water and by adding this solution to 5 ml of the gastric juice of a rat. A precipitate was obtained and the suspension was incubated at 37° C. for 60 minutes with stirring. After this period the precipitate was separated by centrifugation and the supernatant was analysed for its iron content. The amount of iron given up to the gastric juice was 1% of the initial total.

(g) Precipitation of the iron derivative with ammonium sulphate

30% (w/v) of ammonium sulphate was added to a 10% solution (w/v) of the iron derivative prepared in accordance with Example 1. A precipitate of the protein derivative of the iron was obtained and had characteristics identical to its initial characteristics and was still soluble in water. Iron was not present in the solution.

The data given above shows that the complexing capacity of the succinylated proteins with respect to iron is not only typical of succinylated milk proteins but is characteristic of succinylated protein derivatives of varied origins and physiological functions, whether animal or vegetable.

As mentioned above, many animal or vegetable proteins of a non-modified type are suitable for linking with iron. When non-modified milk proteins, ovalbumin, soya proteins, serum proteins, organ extract proteins (liver) are reacted with iron under the conditions described, for the preparation of the corresponding succinyl-protein derivatives, a product is obtained having a similar iron content, but with completely different characteristics of solubility and stability. For example, as shown in Table I, soya protein provides a final product which, when freeze-dried, is insoluble beyond 75% and gives up its iron when treated with gastric juice. In addition to the complexing behaviour with respect to iron, the behaviour of the succinylated ferro-protein derivatives of the invention (i.e. solubility in an alkaline medium, stability in an acid medium and in the presence of gastric juices even at high iron contents) are not attributed to the base proteins and could not therefore be foreseen.

TOXICITY (a) Acute toxicity was tested orally in Swiss mice by gastric probe with respect to the ferrosuccinyl protein of milk proteins, obtained in accordance with Example 1, with distilled water as the carrier. The $LD_{50}$ was greater than 4,000 mg/kg.

(b) The toxicity under repeated administration of the same derivative of Example 1 (indicated below as Ferrolat) in rats, per os, was recorded for 20 days of consecutive treatment on male Wistar rats having an initial weight of 200 g, caged for 14 days before treatment and then separated at random into groups of 10 (Group I: controls; II, III and IV Ferrolat at 30-100-300 mg/kg/die).

The preparation, dissolved at the time of use in distilled water, was administered daily with no gaps at the same time every day by means of a probe. The controls received an equal volume of tap water (10 ml/kg). During treatment, the rats were weighed daily, before administration, and observed for several hours after administration of the product. The food consumption was measured at the end of the treatment, and 24 hours after the final administration, and after a fast of 20 hours the rats were anaesthetized with ether and sacrificed by cutting of the carotid. Part of the blood was collected in a test tube containing EDTA (2 drops of a 4% solution) and the remainder was left as serum. Haemochromocytometric tests were carried out on the total blood and haematochemical tests were carried out on the serum.

RESULTS

Variations in weight and consumption of food

Figure 9:
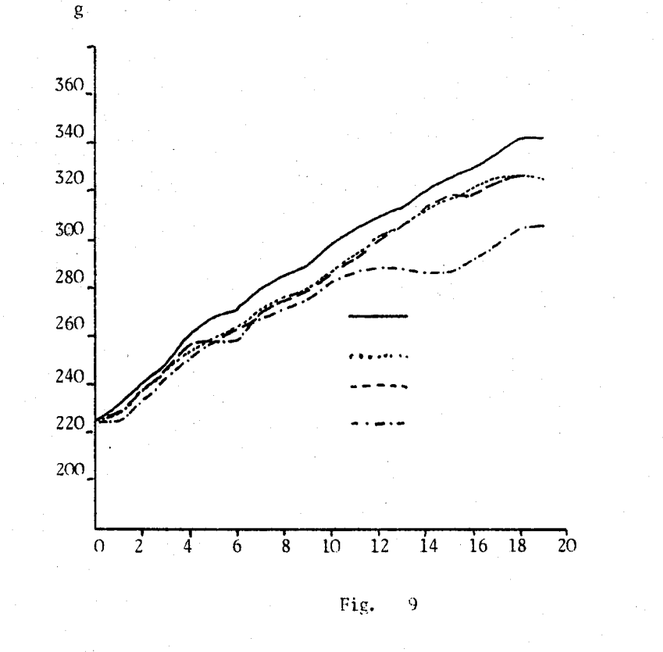

FIG. 9 shows the weight increase curves obtained during treatment until the day preceding the sacrifice.

Tables II and III show the values relating to the weight increase and the food consumption of the animals during treatment.

The weight increase curve of the group of rats treated with Ferrolat at a dosage of 300 mg/kg is shown to be significantly slowed down with respect to the weight increase curve of the control group of rats from the 15th. day following the start of treatment; the same group of rats consumed less food on average ($-11.7\%$).

Slight differences, which are not significant from a statistical point of view, can be observed with respect to the remaining groups of rats treated with Ferrolat.

Haematological tests

The results are shown in table IV.

Haematochemical tests

The results are shown in table V. A slight decrease in the alkaline phosphotase was observed in the rats treated with Ferrolat, 300 mg/kg/die.

Urine tests

The results are shown in table VI.

Organ tests

Table VII shows the absolute average weights of the main rat organs and table VIII with corresponding average weights relating to the body weight.

A significant increase in the relative weight of the spleen and of the lungs was recorded in the group of rats treated with Ferrolat 100 mg/kg/die. In addition to a significant decrease in the body weight, a significant increase in the average weight of the testicles was observed in the group of rats treated with Ferrolat 300 mg/kg/die.

HAEMATIC LEVELS AFTER ORAL ADMINISTRATION (a) Ferrolat-ferrous sulphate comparison Male Wistar rats, weighing approximately 200 grammes and starved for 18 hours were taken, randomized and separated into groups of 5; each group had been sacrificed at the determined hour and blood was taken from each animal by resecting the carotid; the amount of iron in the blood of each animal of the group was determined spectrophotometrically by means of bathophenanthrolinsulphonic acid (Fe-test, Wako). The administration was carried out by a probe in an acqueous solution (5 ml/kg).

The succinyl ferroprotein derivative which was used was prepared as in example 1 (Ferrolat). Dosages and results are shown in table IX. It can be seen that the quantity of iron/kg. was the same for both the derivatives (Fe: 1 mg/kg).

(b) Ferrolat—ferritin comparison

Male Wistar rats, weighing approximately 200 grams and starved for 18 hours, were taken, randomized and separated into groups of 9; each group was sacrificed at the determined hour and blood was taken from each animal by resecting the carotid. The amount of iron in the blood of each animal of the group was determined spectrophotometrically by means of the Iron Colorimetric Method (Boehringer-Mannheim). The administration was carried out by a probe in an acqueous solution (5 ml/kg). Dosages and results are shown in table X. It can be seen that the quantity of iron/kg for the succinyl ferroprotein derivative indicated as Ferrolat was that of ferritin (Sigma, St. Louis, Mo.) and equal to 1 mg/kg.

(c) Comparison between succinyl ferroprotein derivatives obtained from different types of proteins Male Wistar rats, weighing approximately 200 grams and starved for 18 hours, were taken, randomized and separated into groups of 5 (one per dose of derivative and a control group). Each group was sacrificed two hours after administration and, by resecting the carotid, blood was taken from each animal and the iron content in the blood was determined by means of bathophenanthrolinsulphonic acid Fe-test, Wako). The oral administration was carried out by a probe in an aqueous solution (5 ml/kg). The doses of individual derivatives which were used were selected so that 1 mg/kg of Fe was always administered.

Tested products:

(1) succinylated soya proteins + Fe (4.42%)
(2) succinylated ovalbumin + Fe (3.57%)
(3) succinylatad bovine serum proteins + Fe (5.78%)
(4) succinylated milk proteins + Fe (4.5%) (Ferrolat).

The results are shown in table XI.

TABLE I

| PROTEIN SOURCE | SUCCINYLATION (% of groups which may be succinylated) | Fe (% g) | YIELD (% of succinylated protein) | SOLUBILITY at pH > 5 [f] |
|---|---|---|---|---|
| Milk [a] | 95 | 6.7 | 30 | + − |
| Milk [b] | " | 4.6 | 20 | + |
| Milk [c] | " | 3.2 | 18 | + |
| Milk [d] | " | 2.5 | 18 | + |
| Milk [e] | " | 0.8 | 13 | + |
| Lactoproteins | 95 | 4.5 |  | + |
| Ovalbumin | 95 | 3.6 | 33 | + |
| Serum proteins (bovine) | 82 | { 5.8 / 5.5 } | 30 | + − |
| (Soya) | 92 | 4.4 | 22 | + |
| (Organ) (Liver) | n.a. | 8.4 | n.a. | + − |
| Milk | 35 | 4.3 | 26 | + |
| Lactoproteins | 0 | 4.8 |  | − |
| Ovaloumin | 0 | { 7.7 / 0.4 } |  | + |
| Soya | 0 | { 4.5 / 0.4 } |  | − / + − |
| Serum proteins (bovine) | 0 | 0.5 |  | + − |
| (Organ) (liver) | 0 | n.a. | n.a. | − |

[a],[b],[c],[d],[e] samples with ratios $Fe^{3+}$:succinylated proteins between 0.1:1 and 5:1 (W:W).
[f] complete (+); partial (+ −); insoluble (−)

TABLE II

| | WEIGHT INCREASE | | |
|---|---|---|---|
| TREATMENT mg/kg/die | Initial average weight | Final average weight | Weight increase average ± SE |
| Controls | 224.10 ± 2.83 | 343.60 ± 8.87 | 119.50 ± 7.66 |
| Ferrolat 30 | 224.40 ± 3.03 | 325.50 ± 4.56 | 101.20 ± 4.35 |
| Ferrolat 100 | 224.40 ± 2.30 | 326.10 ± 8.06 | 101.70 ± 8.08 |
| Ferrolat 300 | 224.30 ± 3.71 | 307.00 ± 10.15* | 82.77 ± 8.28** |

*$p < 0.05$
**$p < 0.01$
Significance with respect to controls (calculated with Student's 't')

TABLE III

| | FOOD CONSUMPTION | |
|---|---|---|
| TREATMENT mg/kg/die | Total average consumption | Variation |
| Controls | 32.33 | — |
| Ferrolat 30 | 30.42 | −5.91 |
| Ferrolat 100 | 30.98 | −4.18 |
| Ferrolat 300 | 28.54 | −11.72 |

TABLE IV

| HAEMATOLOGICAL DATA | | | | |
|---|---|---|---|---|
| TREATMENT | | | mg/kg/die | |
| | Controls | Ferrolat 30 | Ferrolat 100 | Ferrolat 300 |
| Haemoglobin g % | 12.11 ± 0.47 | 11.77 ± 0.37 | 12.39 ± 0.30 | 12.93 ± 0.25 |

TABLE IV-continued

HAEMATOLOGICAL DATA

| TREATMENT | | | mg/kg/die | |
|---|---|---|---|---|
| | Controls | Ferrolat 30 | Ferrolat 100 | Ferrolat 300 |
| Haematocrit % | 66.88 ± 2.06 | 61.44 ± 1.96 | 66.90 ± 2.77 | 64.16 ± 1.80 |
| Leucocytes $10^3$ $mm^3$ | 16.95 ± 2.25 | 16.55 ± 1.65 | 23.46 ± 2.16 | 19.93 ± 2.58 |
| Erythrocytes $10^6/mm^3$ | 5.76 ± 0.51 | 6.12 ± 0.68 | 5.91 ± 0.68 | 6.22 ± 0.31 |

TABLE V

HAEMATOCHEMICAL DATA

| TREATMENT | | | mg/kg/die | |
|---|---|---|---|---|
| | Controls | Ferrolat 30 | Ferrolat 100 | Ferrolat 300 |
| Glucose mg % | 55.33 ± 5.75 | 52.81 ± 4.38 | 63.61 ± 5.58 | 60.74 ± 4.97 |
| Azotemia mg % | 32.73 ± 1.33 | 34.59 ± 2.25 | 28.68 ± 2.34 | 32.33 ± 2.52 |
| GOT mU/ml | 110.51 ± 7.10 | 130.81 ± 8.59 | 109.09 ± 5.21 | 113.36 ± 7.29 |
| GPT mU/ml | 19.58 ± 1.52 | 26.86 ± 3.43 | 30.14 ± 6.02 | 23.15 ± 2.57 |
| Alkaline phosphatase mU/ml | 255.65 ± 13.82 | 229.53 ± 17.03 | 257.53 ± 22.35 | 213.80 ± 12.72* |
| Total proteins g % | 6.19 ± 0.12 | 6.02 ± 0.17 | 6.37 ± 0.12 | 6.21 ± 0.16 |

Significance
*$p < 0.05$
**$p < 0.01$
***$p < 0.001$

TABLE VI

URINE TESTS

| TREATMENT | | | mg/kg/die | |
|---|---|---|---|---|
| | Controls | Ferrolat 30 | Ferrolat 100 | Ferrolat 300 |
| pH | 8.15 ± 0.17 | 8.55 ± 0.14 | 8.40 ± 0.18 | 8.50 ± 0.12 |
| proteins | 21.- ± 3.78 | 24.- ± 3.05 | 63.- ± 12.47** | 53.33 ± 11.66* |
| glucose | nil | nil | nil | nil |
| ketone bodies | nil | nil | nil | nil |
| bilirubin | nil | nil | nil | nil |
| blood | nil | nil | nil | nil |

Significance
*$p < 0.05$
**$p < 0.01$
***$p < 0.001$

TABLE VII

ABSOLUTE FRESH WEIGHT OF THE RATS' ORGANS

| TREATMENT | | | mg/kg/die | |
|---|---|---|---|---|
| | Controls | Ferrolat 30 | Ferrolat 100 | Ferrolat 300 |
| Body weight g | 310.60 ± 7.53 | 300.33 ± 3.64 | 296.8 ± 6.16 | 278.44 ± 8.89* |
| Heart g | 1.15 ± 0.05 | 1.10 ± 0.03 | 1.14 ± 0.04 | 1.09 ± 0.07 |
| Lungs g | 1.55 ± 0.05 | 1.70 ± 0.20 | 1.68 ± 0.05 | 1.57 ± 0.12 |
| Liver g | 9.14 ± 0.35 | 8.89 ± 0.35 | 8.78 ± 0.28 | 8.35 ± 0.44 |
| spleen g | 1.38 ± 0.13 | 1.36 ± 0.08 | 1.65 ± 0.12 | 1.37 ± 0.09 |
| Kidneys g | 2.28 ± 0.07 | 2.21 ± 0.09 | 2.22 ± 0.08 | 2.09 ± 0.10 |
| Surrenal glands mg | 50.30 ± 4.55 | 56.33 ± 7.69 | 51.80 ± 6.07 | 37.44 ± 5.56 |
| Brain g | 1.77 ± 0.03 | 1.70 ± 0.03 | 1.67 ± 0.05 | 1.68 ± 0.06 |
| Testicles g | 3.30 ± 0.05 | 3.12 ± 0.10 | 3.08 ± 0.16 | 3.25 ± 0.07 |
| Stomach g | 1.77 ± 0.09 | 1.77 ± 0.05 | 1.75 ± 0.07 | 1.53 ± 0.09 |

Significance
*$p < 0.05$
**$p < 0.01$
***$p < 0.001$

TABLE VIII

RELATIVE FRESH WEIGHT OF THE RATS' ORGANS

| TREATMENT | | | mg/kg/die | |
|---|---|---|---|---|
| | Controls | Ferrolat 30 | Ferrolat 100 | Ferrolat 300 |
| Body weight | 310.60 ± 7.53 | 300.33 ± 3.64 | 296.80 ± 6.16 | 278.44 ± 8.89* |
| Heart % | 0.37 ± 0.01 | 0.37 ± 0.08 | 0.39 ± 0.09 | 0.39 ± 0.02 |
| Lungs % | 0.50 ± 0.02 | 0.56 ± 0.06 | 0.57 ± 0.02* | 0.57 ± 0.06 |
| Liver % | 2.94 ± 0.04 | 2.96 ± 0.10 | 2.96 ± 0.06 | 2.99 ± 0.08 |

TABLE VIII-continued

RELATIVE FRESH WEIGHT OF THE RATS' ORGANS

| TREATMENT | | mg/kg/die | |
|---|---|---|---|
| | Controls | Ferrolat 30 | Ferrolat 100 | Ferrolat 300 |
| Spleen % | 0.44 ± 0.03 | 0.45 ± 0.03 | 0.56 ± 0.04* | 0.49 ± 0.03 |
| Kidneys % | 0.73 ± 0.01 | 0.74 ± 0.02 | 0.75 ± 0.03 | 0.75 ± 0.02 |
| Surrenal glands % | 0.016 ± 0.001 | 0.019 ± 0.003 | 0.017 ± 0.002 | 0.014 ± 0.002 |
| Brain % | 0.57 ± 0.02 | 0.57 ± 0.01 | 0.57 ± 0.02 | 0.60 ± 0.01 |
| Testicles % | 1.06 ± 0.02 | 1.04 ± 0.03 | 1.04 ± 0.05 | 1.18 ± 0.04* |
| Stomach % | 0.56 ± 0.02 | 0.59 ± 0.02 | 0.59 ± 0.02 | 0.54 ± 0.02 |

Significance
*$p < 0.05$
**$p < 0.01$
***$p < 0.001$

TABLE IX

HAEMATIC LEVELS: COMPARISON FERROLAT - FERROUS SULPHATE

| TREATMENT | Serum iron µg % hours after treatment | | | | |
|---|---|---|---|---|---|
| | 30' | 1 | 2 | 4 | 6 |
| Controls H₂O 5 ml/kg | 99.22 ± 24.92 (5) | 59.91 ± 6.85 (5) | 98.23 ± 13.28 (5) | 80.17 ± 6.37 (5) | 74.— ± 10.10 (5) |
| Ferrolat; 22.37 mg/kg (Fe = 1 mg/kg) | 227.45** ± 16.40 (5) | 275.28*** ± 18.91 (5) | 269.61*** ± 22.51 (5) | 203.16** ± 27.74 (5) | 148.18** ± 16.75 (5) |
| FeSO₄7H₂O: 4.98 mg/kg (Fe = 1 mg/kg p.os) | 336.27*** ± 27.79 (5) | 272.14*** ± 24.09 (5) | 273.56*** ± 19.32 (5) | 129.50*** ± 6.21 (5) | 80.52 ± 5.65 (5) |

Significance with respect to controls:
*$p < 0.05$
**$p < 0.01$
***$p < 0.001$
Significance of the two iron preparations:
30': $p < 0.01$; 4h: $p < 0.05$; 6h: $p < 0.01$

TABLE X

HAEMATIC LEVELS: COMPARISON FERROLAT - FERRITIN

| TREATMENT | Serum iron µg/100 ml hours after treatment | | | |
|---|---|---|---|---|
| | 1 | 2 | 4 | 6 |
| Ferritin (F-4503 Sigma dilution 1.08% v/v, 5 ml/kg = 1 mg/kg di Fe) | 168.79 ± 15.35 | 170.66 ± 14.70 | 148.08 ± 18.69 | 89.22 ± 12.75 |
| Ferrolat 21.46 mg/kg (= 1 mg/kg di Fe) in 5 ml/kg | 302.07*** ± 15.59 | 269.81** ± 29.94 | 223.72 ± 18.51 | 106.24 ± 11.30 |
| Controls, distilled 5 ml/kg | 80.40*** ± 6.39 | | | |

*$p < 0.05$
**$p < 0.01$
***$p < 0.001$
Significance calculated with Student "t" with respect to ferritin.

TABLE XI

BLOOD LEVELS: COMPARISON BETWEEN SUCCINYL FERROPROTEINS OBTAINED FROM DIFFERENT TYPES OF PROTEINS

| TREATMENT | serum iron in µg/100 ml average values ± SE |
|---|---|
| Controls | 83.99 ± 7.56 |
| Succ. soya | 260.68 ± 29.52*** |
| Succ. ovalbumin | 235.82 ± 46.06* |
| Succ. serum protein | 277.63 ± 49.35** |
| Ferrolat | 305.81 ± 23.20*** |

Significance with respect to the controls
*$p < 0.05$
**$p < 0.01$
***$p < 0.001$ The present invention also relates to all the applicable industrial aspects involved in the use of succinyl ferroprotein derivatives described and claimed here as agents suitable for the treatment of sideropenic anaemia. An essential aspect of the invention therefore consists in pharmaceutical formulations for human and veterinary use containing predetermined quantities of these derivatives. The latter can be administered orally, for example in the form of tablets, capsules, ampoules; sachets containing granulates; syrups; powders to add to animal food; etc.

The following formulations are given purely by way of example:
    ampoules containing 5-10-40 mg of iron in the form of ferro succinyl proteins, in addition to acqueous solvents, stabilizers, flavouring agents etc. as commonly used in pharmacy;

tablets from 5-10-40 mg of iron in the form of ferrosuccinyl proteins, in addition to excipients, dispersing agents etc. commonly used in pharmaceutics;

capsules from 5-10-40 mg of iron in the form of ferrosuccinyl proteins;

unit dose sachets containing an effervescent granulate equal to 5-10-40 mg of iron in the form of ferro proteins, in addition to sugar, flavouring agents, stabilizers etc. commonly used in pharmacy;

powdered milk to be added to weaning animal food, at 5% to 20% by weight of active principle.

We claim:

1. A bio-available succinyl ferro-protein derivative obtained by reacting a succinylated animal or vegetable protein with ferro ions.

2. A bio-available succinyl ferro-protein derivative according to claim 1 in which the ferro content is about 0.1–20% by weight.

3. A bio-available succinyl ferro-protein derivative according to claim 2 in which the degree of succinylation of the protein is from about 20 to 100%.

4. A bio-available succinyl ferro-protein derivative according to claim 3 in which the degree of succinylation is greater than 70% and the ferro content is greater than 4% by weight.

5. A bio-available succinyl ferro-protein derivative according to claim 4 in which the protein is a milk protein.

6. A bio-available succinyl ferro-protein derivative according to claim 4 in which the protein is an ovalbumin protein.

7. A bio-available succinyl ferro-protein derivative according to claim 4 in which the protein is a soya protein.

8. A method for preparing a bio-available succinyl ferro-protein derivative which comprises reacting a succinylated animal or vegetable protein with a ferro salt in an aqueous medium at a pH of about 2–10 and isolating the resultant reaction product by precipitation at a pH of about 2-4 produced spontaneously or by acidification.

9. A method according to claim 8 in which the reaction between the succinylated protein and the ferro salt is conducted at a pH of about 7.

10. A method for preparing a bio-available succinyl ferro-protein derivative which comprises reacting a succinylated animal or vegetable protein with a ferro salt in an aqueous medium at a pH of about 2–10 and isolating the resultant reaction product by separating the aqueous medium after adjusting the pH to about 7.

11. A pharmaceutical composition for treating sideropenic anaemia in animals and humans containing as the active ingredient an effective amount of a bio-available succinyl ferro animal or vegetable protein derivative in admixture with a pharmaceutically acceptable carrier.

* * * * *